US011969573B2

(12) United States Patent
Okihara

(10) Patent No.: US 11,969,573 B2
(45) Date of Patent: Apr. 30, 2024

(54) MEDICAL DEVICE PACKAGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 104 days.

(21) Appl. No.: 17/186,787

(22) Filed: Feb. 26, 2021

(65) Prior Publication Data

US 2021/0268169 A1 Sep. 2, 2021

(30) Foreign Application Priority Data

Feb. 27, 2020 (JP) ................................. 2020-031412

(51) Int. Cl.
*A61M 5/00* (2006.01)
*B65B 3/00* (2006.01)
(Continued)

(52) U.S. Cl.
CPC .............. *A61M 5/002* (2013.01); *B65B 3/003* (2013.01); *B65D 25/108* (2013.01); *B65D 51/18* (2013.01);
(Continued)

(58) Field of Classification Search
CPC ..... A61M 5/002; A61M 5/008; B65D 25/108; B65D 51/18; B65D 2251/0031;
(Continued)

(56) References Cited

U.S. PATENT DOCUMENTS 4,423,732 A * 1/1984 Tarjan .................. A61N 1/3752
607/27
4,671,943 A * 6/1987 Wahlquist ................. A61L 2/26
220/849
(Continued)

FOREIGN PATENT DOCUMENTS

JP H11-506995 A 6/1999
JP 2008-505029 A 2/2008
(Continued)

OTHER PUBLICATIONS

The European Search Report issued Jul. 30, 2021, by the European Patent Office in corresponding European Patent Application No. 21158341.4-1122. (4 Pages).
(Continued)

*Primary Examiner* — J. Gregory Pickett
*Assistant Examiner* — Jenine Pagan
(74) *Attorney, Agent, or Firm* — BUCHANAN INGERSOLL & ROONEY PC

(57) ABSTRACT

A medical device package includes: a medical device container including a nest which holds a plurality of medical devices (syringes) to be filled with medicine to be aligned in a predetermined direction, a medical device container main body which accommodates the nest, and a sheet-shaped first sealing member which seals the medical device container main body; and a storage container for packing with an outer peripheral surface of the medical device container maintained in a sterile state. The storage container is formed of a storage container main body accommodating the medical device container and having a shape-retaining property, and seals a transfer opening at an upper end of the storage container main body with a sheet-shaped second sealing member having an antibacterial property and air permeability.

20 Claims, 13 Drawing Sheets

(51) Int. Cl.
  *B65D 25/10* (2006.01)
  *B65D 51/18* (2006.01)
(52) U.S. Cl.
  CPC ............... *B65D 2251/0031* (2013.01); *B65D 2251/0093* (2013.01)
(58) Field of Classification Search
  CPC ........ B65D 2251/0093; B65D 77/0446; B65D 77/0453; B65D 81/28
  USPC ....... 206/364, 366, 365, 438, 461, 499, 518, 206/514, 515, 516, 509, 520, 501, 363, 206/439, 585, 588, 589, 443; 220/23.83, 220/23.86, 23.88, 23.89, 512, 446, 507; 211/85.17, 70.1, 74, 60.1
  See application file for complete search history.

(56) References Cited

U.S. PATENT DOCUMENTS

| | | | |
|---|---|---|---|
| 5,590,778 | A | 1/1997 | Dutchik |
| 6,830,149 | B2* | 12/2004 | Merboth ............... A01N 1/0263 206/461 |
| 7,249,686 | B1* | 7/2007 | Aesquivel ............ B65D 81/262 206/514 |
| 2005/0224382 | A1* | 10/2005 | Raynal-Olive ......... A61L 2/208 206/524.1 |
| 2006/0016156 | A1 | 1/2006 | Bush et al. |
| 2009/0100802 | A1* | 4/2009 | Bush ...................... A61M 5/002 53/434 |
| 2014/0353190 | A1* | 12/2014 | Okihara ................. B65B 55/10 206/370 |
| 2017/0247132 | A1 | 8/2017 | Deutschle et al. |
| 2021/0008285 | A1 | 1/2021 | Okihara |

FOREIGN PATENT DOCUMENTS

| | | | |
|---|---|---|---|
| JP | 2012-071046 | A | 4/2012 |
| JP | 2016-073377 | A | 5/2016 |
| JP | 2017080478 | A | 5/2017 |
| WO | 2014/049712 | A1 | 4/2014 |
| WO | 2016/166765 | A1 | 10/2016 |
| WO | 2019/189385 | A1 | 10/2019 |

OTHER PUBLICATIONS

Office Action (Notice of Reasons for Refusal) dated Jun. 20, 2023, by the Japan Patent Office in corresponding Japanese Patent Application No. 2020-031412 and an English translation of the Office Action. (8 pages).

* cited by examiner

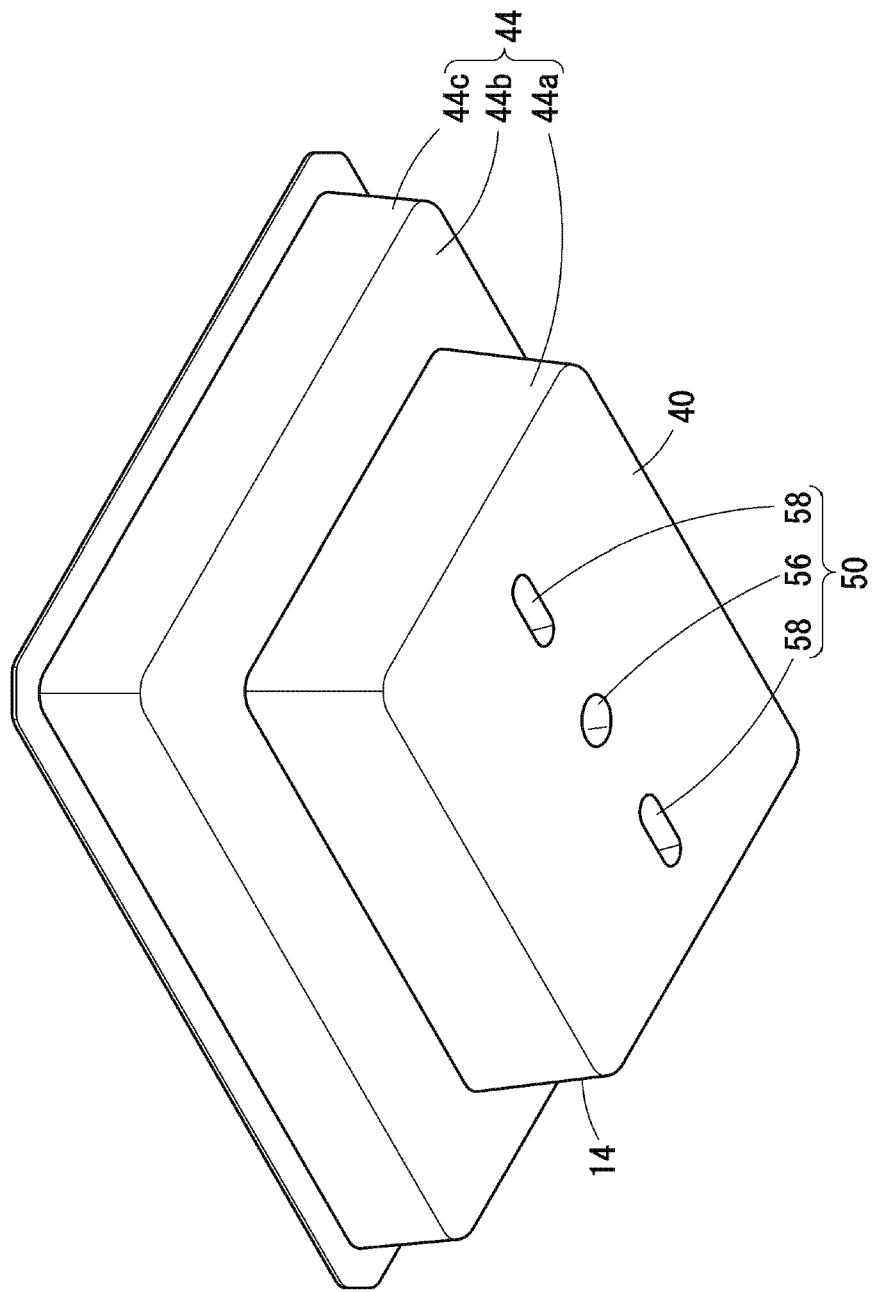

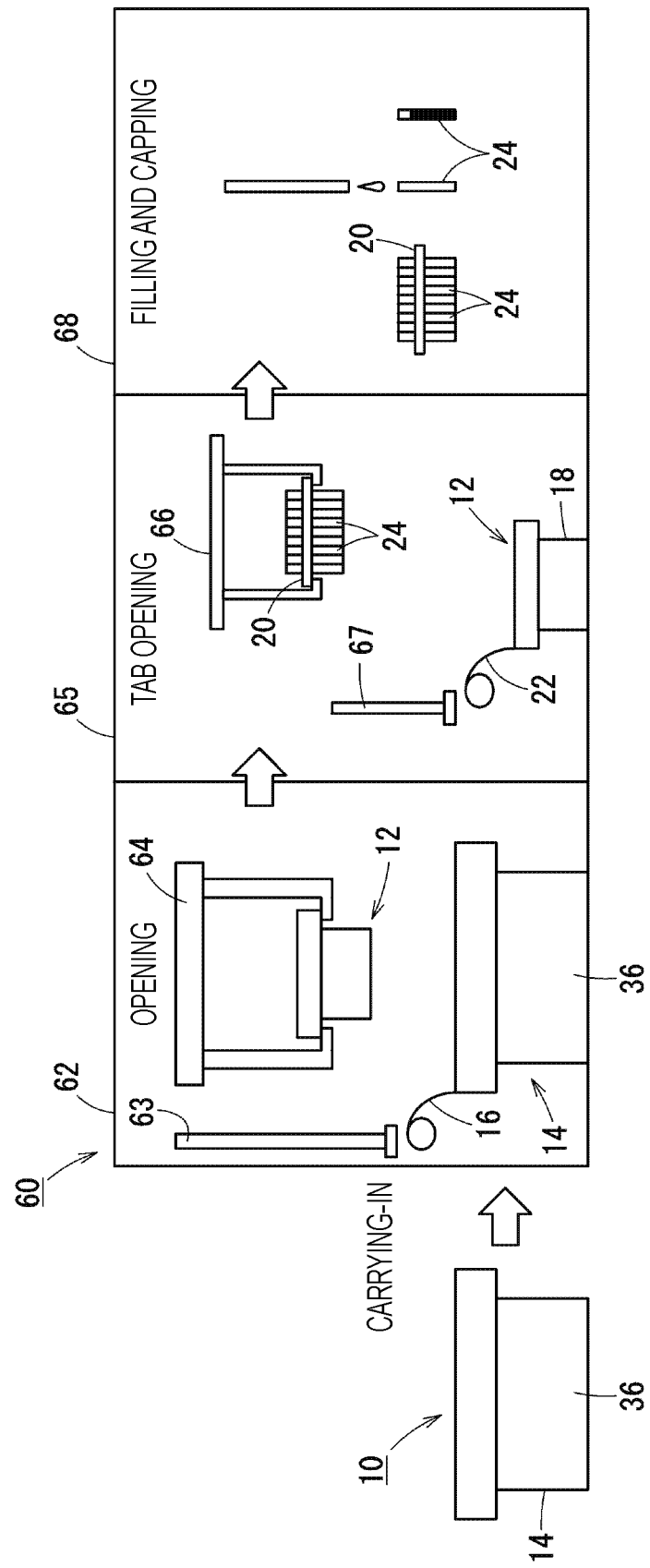

MEDICAL DEVICE PACKAGE

CROSS-REFERENCES TO RELATED APPLICATIONS

This application claims priority to Japanese Patent Application No. 2020-031412 filed on Feb. 27, 2020, the entire content of which is incorporated herein by reference.

FIELD OF THE INVENTION

The present invention generally relates to a medical device package and method of filling medical device.

BACKGROUND DISCUSSION

In the medical field, products filled with medicines are used in medical devices such as vials, cartridges, and syringes. For example, a product in which a syringe is filled with a medicine is known as a prefilled syringe.

Such manufacturing of medical devices and filling of the medical devices with medicines are generally performed at different locations. Therefore, as illustrated in Japanese Patent Application Publication No. 2017-80478, a plurality of medical devices are collectively held in a holder called a nest, and the nest is sealed and transferred in a container called a tab.

The tab is transferred to a medicine filling facility and carried into a drug filling device. The drug filling device performs a series of steps including a step of opening the tab and taking out the medical devices, a step of filling the medical devices with medicines, and a step of capping the medical devices in an unattended manner in a sterile environment. At that time, in order to maintain the sterility of the drug filling device, an outer surface of the tab to be carried in is also required to be sterile.

Typically, the tab is stored in a sterilized bag and distributed, and the outer surface of the tab is also set to a sterile state. However, the sterilized bag is made of a thin resin film, and thus, is vulnerable to a breakage and is likely to cause a pinhole and contamination. Therefore, irradiation sterilization is performed by radiation irradiation before and after the opening of the sterilized bag in the drug filling device.

However, the irradiation sterilization requires a considerable amount of irradiation time, which slows down the processing speed. Therefore, there is a problem that it is difficult to perform the irradiation sterilization in a high-speed drug filling device. Therefore, a method a method is employed that involves doubling the sterilized bag in order to maintain the sterility of the outer surface of the tab at the time of transferring the tab used in the high-speed drug filling device.

SUMMARY

The tab is taken out from the sterilized bag by an operation of opening the outer sterilized bag and taking out the inner sterilized bag in which the tab has been placed, from the outer sterilized bag, and an operation of opening the inner sterilized bag and taking out the tab from the inner sterilized bag, and these operations are automatically performed by an opening device. At this time, there is a problem that the inner sterilized bag is hardly handled with the opening device.

That is, when the inner sterilized bag is stored in the outer sterilized bag, creases and wrinkles are inevitably generated therein, and a shape is not constant. Therefore, when taking out the inner sterilized bag with a suction-type chuck device, there may occur events such as a suction error due to suction of a wrinkled portion and a gripping failure due to poor positioning by a transfer device using an arm. As a result, the drug filling device is stopped, which causes a problem that the productivity is lowered.

The medical device package disclosed here exhibits excellent ability to maintain sterility on an outer surface of a medical device container and to be handled by a machine.

One aspect of the disclosure involves a medical device package comprising: a medical device container including a nest holding a plurality of medical devices aligned in a predetermined direction and configured to be filled with medicine, with the medical device container also including a medical device container main body in which the nest is accommodated and a sheet-shaped first sealing member sealing the medical device container main body; and a storage container. The storage container includes a storage container main body in which is accommodated the medical device container in a sterile state, wherein the storage container main body has a shape-retaining property, a through opening at one end of the storage container main body to permit the medical device container to be introduced into the storage container main body and to be removed from the storage container main body, and a sheet-shaped second sealing member sealing the through opening at the one end of the storage container main body, with the sheet-shaped second sealing member having an antibacterial property and air permeability.

According to the medical device package from the above viewpoint, the medical device container is accommodated in the storage container and sealed with the second sealing member, the sterility of the outer peripheral surface of the medical device container can be maintained. Since the storage container does not break or wrinkle like a sterilized bag, the handleability by the machine is improved.

According to another aspect, a medical device package comprises: a nest in which are held plural medical devices each of which is to be filled with medicine, with each of the plural medical devices having an open upper end and a closed bottom end; a medical device container main body that includes an accommodation space in which is positioned the nest and the plural medical devices, with the accommodation space of the medical device container main body being surrounded by a bottom of the medical device container main body and by an upstanding side wall of the medical device container main body that extends upwardly away from the bottom of the medical device container main body when the nest and the medical devices are accommodated in the accommodation space of the medical device container main body. The medical device container main body includes an opening that communicates with the accommodation space of the medical device container main body to permit the nest and the medical devices to be introduced into the accommodation space of the medical device container main body and to be removed from the accommodation space of the medical device container main body. A sheet-shaped first seal covers the opening in the medical device container main body to seal the medical device container main body, and the sheet-shaped first seal is removable to uncover the opening in the medical device container main body and permit the nest and the medical devices to be removed from the accommodation space of the medical device container main body. The medical device package also comprises a storage container main body that includes an accommodation space in which is positioned the medical device container main body in a sterile state, with the accommodation space of the storage container main body being surrounded by a support portion of the storage container main body and an upstanding peripheral wall portion of the storage container main body that extends upwardly away from the support portion of the storage container main body when the medical device container main body is accommodated in the accommodation space of the storage container main body. The support portion of the storage container main body faces the bottom of the medical device container main body, and the storage container main body includes an opening that communicates with the accommodation space of the storage container main body to permit the medical device container main body to be introduced into the accommodation space of the storage container main body and to be removed from the accommodation space of the storage container main body. A sheet-shaped second seal covers the opening in the storage container main body to seal the storage container main body, the sheet-shaped second seal is removable to uncover the opening in the storage container main body and permit the medical device container main body to be removed from the accommodation space of the storage container main body, and the sheet-shaped second seal has an antibacterial property and being air permeable.

In accordance with another aspect, a method of filling medical devices with medicine comprises: introducing a medical device package into a drug filling device, wherein the medical device package comprises a storage container main body that includes an accommodation space in which is accommodated a medical device container main body that is in a sterile state, with the medical device container main body including an accommodation space in which is accommodated the medical devices held by a nest, and the medical devices having open upper ends, the medical device container main body including a bottom wall that faces a support portion of the storage container main body. The method also comprises at least partially removing a sealing member that covers a through opening in the storage container main body to uncover the through opening in the storage container main body and permit access to the accommodation space in the storage container main body, and removing the medical device container main body from the accommodation space in the storage container main body by way of the through opening in the storage container main body, with the medical device container main body being removed from the accommodation space in the storage container main body while a peripheral wall of the storage container main body is upstanding and extending away from the support portion of the storage container main body. Additionally, the method involves at least partially removing a sealing member that covers a through opening in the medical device container main body to uncover the through opening in the medical device container main body and permit access to the accommodation space in the medical device container main body in which are located the medical devices, and introducing the medicine into the open upper ends of the medical devices.

BRIEF DESCRIPTION OF THE DRAWINGS

FIG. 5 is an explanatory view of a second positioning structure of the medical device package of FIG. 1.

FIG. 7 is an explanatory view of a drug filling device to which the medical device package of FIG. 1 is applied.

DETAILED DESCRIPTION

Set forth below with reference to the accompanying drawings is a detailed description of embodiments of a medical device package and method of filling a medical device representing examples of the inventive medical device package and medical device filling method disclosed here.

First Embodiment

Figure 1:
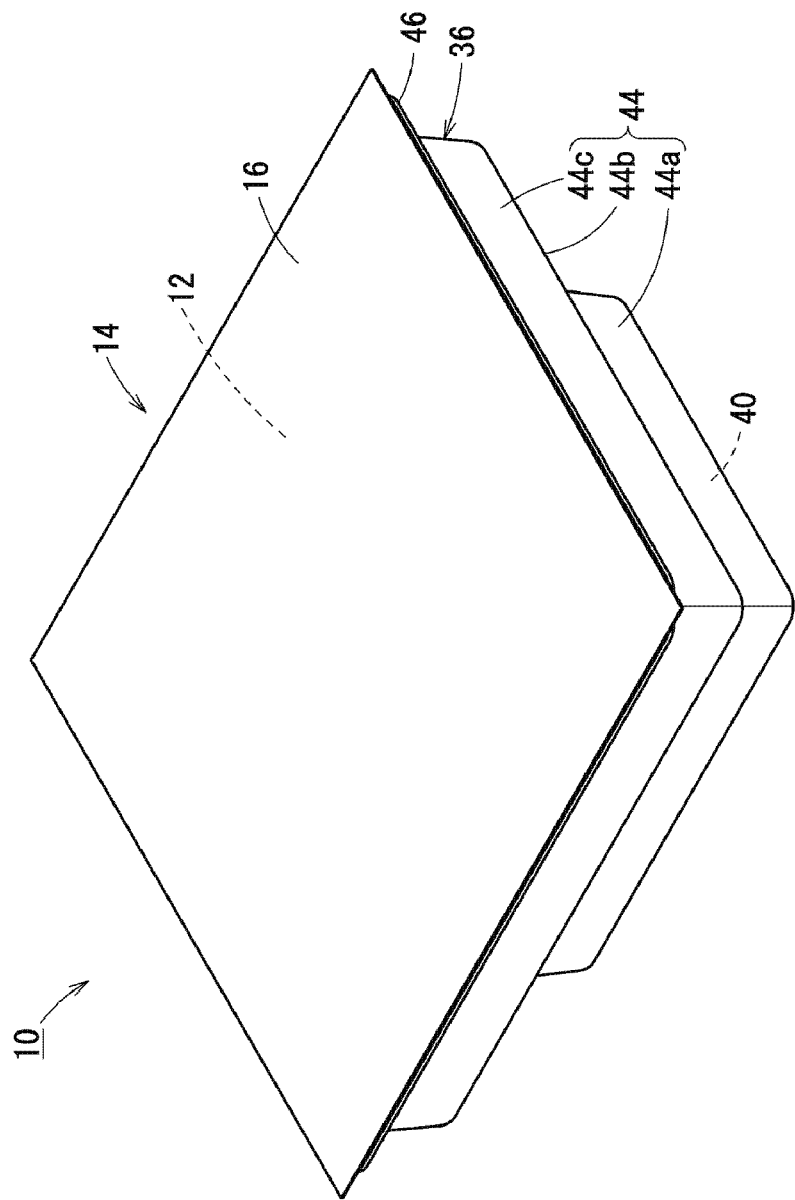
FIG. 1 is a perspective view of a medical device package according to a first embodiment.
Figure 2:
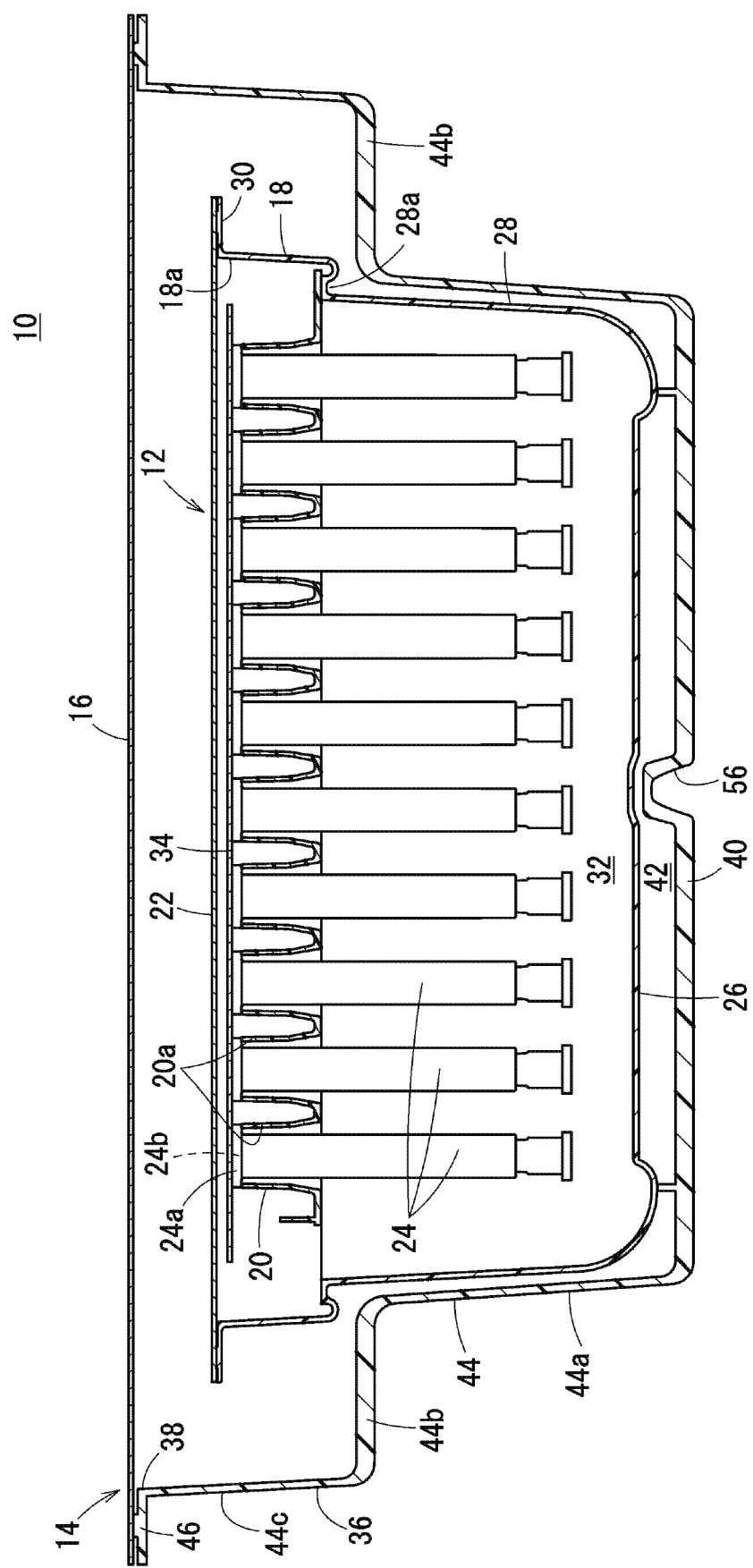
FIG. 2 is a cross-sectional view of the medical device package of FIG. 1.
Figure 3:
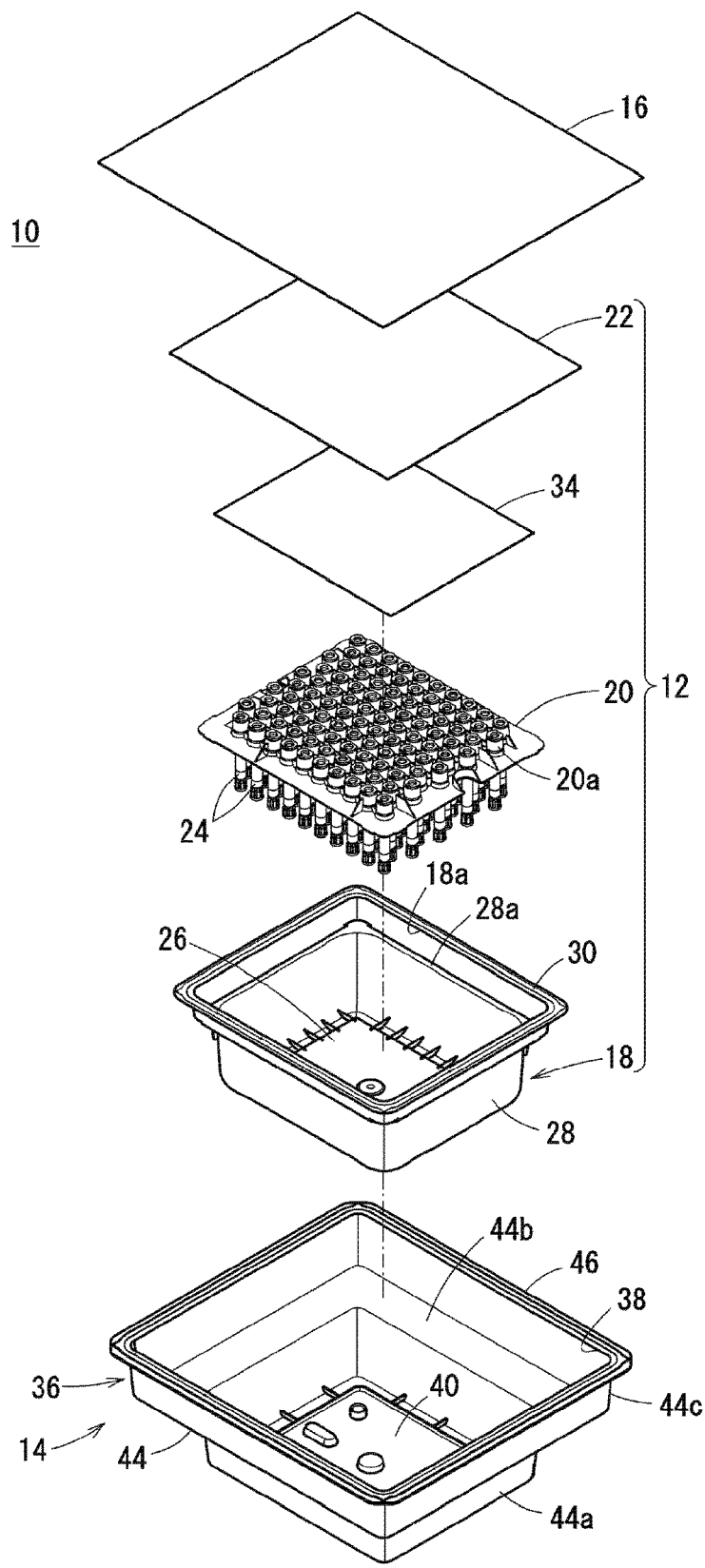
FIG. 3 is an exploded perspective view of the medical device package of FIG. 1.

As illustrated in FIGS. 1 to 3, a medical device package 10 according to one embodiment includes a medical device container 12 accommodating a medical device, and a storage container 14 accommodating the medical device container 12. The storage container 14 is configured to maintain a sterilized state on an outer peripheral surface of the medical device container 12 by being sealed by the second sealing member 16 in the state of accommodating the medical device container 12. That is, the medical device container 12 with its outer periphery in a sterilized state is accommodated or positioned in the interior of the storage container 14, and the interior of the storage container 14 is sealed by the second sealing member 16 while the medical device container 12 (with its outer periphery in a sterilized state) is located in the interior of the storage container 14.

The medical device container 12 is a container configured to store and transfer the medical device while keeping the medical device in the sterilized state, and includes a medical device container main body 18, a nest 20 held by the medical device container main body 18, and a first sealing member 22. The nest 20 is a plate-shaped holder that holds a plurality of medical devices in bundle or as a group, and a plurality of openings (through openings) 20a in the plate-shaped holder each configured to receive and hold a syringe outer cylinder, a vial bottle, a cartridge, and the like. In the present embodiment, one possibility will be described in which a syringe 24, representing one example of the medical device, is accommodated in the medical device container. The description below applies to all of the medical devices or syringes 24 of the medical device container 12. The syringe 24 is inserted into or positioned in the opening 20a of the nest 20 and is held in the nest 20 by virtue of a flange 24a of the syringe 24 being hooked by the opening 20*a* of the nest 20 so that the flange portion 24*a* of the syringe is supported on the portion of the plate-shaped holder surrounding the opening 20*a*.

The medical device container main body 18 is a concave-shaped container (e.g., a container that is recessed as shown in FIG. 3) formed in a rectangular shape in a plan view, and includes an integrally formed bottom portion 26, an upstanding side wall 28, and a flange portion (flange) 30. The bottom portion 26 is formed in a flat rectangular shape in a plan view. The side wall 28 extends upward from a peripheral edge of the bottom portion 26. The flange portion 30 is provided at an upper end of the side wall 28. An accommodation space 32 to accommodate the nest 20 is surrounded by the bottom portion 26 and the side wall 28 of the medical device container main body 18. An opening 18*a* configured to insert and take out the nest 20 is formed at an upper end of the medical device container main body 18, meaning the upper end of the medical device container main body 18 is an open upper end. The flange portion 30 extends outward from an upper end of the side wall 28 so that the flange portion extends away from the accommodation space 32. The flange portion 30 is formed along a plane parallel to the bottom portion 26, and the first sealing member 22 is joined to the flange portion 30 (e.g., the upwardly facing surface of the flange portion 30 as shown by way of example in FIG. 2).

The nest 20 is accommodated or located inside the medical device container main body 18 in the state in which the nest 20 holds the plurality of syringes 24. The medical device container main body 18 is formed with a step portion (step) 28*a* near the upper end of the side wall 28 in order to hold the nest 20. The step portion 28*a* is formed by bending the side wall 28 so as to extend outward and form a shoulder or shelf that supports an outer peripheral portion of the nest 20. As illustrated in FIG. 2, when the nest 20 is placed on or supported by the step portion 28*a*, the nest 20 is positioned in the medical device container main body 18 (i.e., in the accommodation space 32 of the medical device container main body 18), and the syringes 24 are held by the nest in the state of being separated from the bottom portion 26 and the side wall 28 of the medical device container main body 18. That is, the medical devices or syringes may be spaced from and not in contact with the bottom portion 26 and the side wall 28 of the medical device container main body 18.

An inner sheet 34 is arranged on the flanges 24*a* of the plurality of syringes 24 held in the nest 20. The inner sheet 34 is a rectangular sheet-like or sheet-shaped member, and is formed in a size that covers filling openings 24*b* of all the syringes 24. The inner sheet 34 is made of a material that an air permeability that allows a sterilization gas (for example, water vapor, an ethylene oxide gas, and the like) to permeate, and has an antibacterial property that prevents permeation of microorganisms such as bacteria and viruses. Examples of the material constituting the inner sheet 34 include Tyvek (registered trademark), which is a high-density polyethylene non-woven fabric manufactured by DuPont.

The first sealing member 22 is removably joined to the flange portion 30 of the medical device container main body 18 accommodating the nest 20 and the syringes 24 by heat welding or adhesion. The first sealing member 22 may be made of the same material as the inner sheet 34. The medical device container 12 is kept in the state of being sealed by the first sealing member 22 until filling of the syringes 24 is performed. The first sealing member 22 is removed when the syringes 24 are filled with a drug by a drug filling device 60 (see FIG. 7).

As illustrated in FIG. 1, the storage container 14 is a box-shaped container formed in a concave shape (i.e., a recessed container), and includes a storage container main body 36 made of a resin material having a shape-retaining property or the like, and a second sealing member 16 that seals a transfer opening (through opening) 38 of the storage container main body 36. The storage container main body 36 includes a flat support portion 40 that constitutes a bottom, and an upstanding peripheral wall portion 44. The support portion 40 together with the upstanding peripheral wall portion 44 form an accommodation space 42 to accommodate the medical device container 12. The support portion 40 is formed in a rectangular shape when viewed in a plan view from above, and supports the bottom portion 26 of the medical device container 12 from below.

The support portion 40 has a first positioning structure 48 (see FIG. 4) that positions the medical device container 12 at a predetermined position in the storage container 14. The medical device container 12 is positioned in the accommodation space 42 at a position separated or spaced from the peripheral wall portion 44 by the first positioning structure 48. Details of the first positioning structure 48 will be described later.

The peripheral wall portion 44 includes a lower portion (lower upstanding portion) 44*a* that rises upward from the support portion 40, a step portion 44*b* that bends or extends outward and extends from an upper end of the lower portion 44*a*, and an upper portion (upper upstanding portion) 44*c* that bends or extends upward from the step portion and rises from an outer edge of the step portion 44*b*. When the medical device container 12 is positioned in the storage container 14, the step portion 44*b* of the storage container 14 is located below the step portion 28*a* of the medical device container 12 accommodated in the storage container 14, and forms a gap around the step portion 28*a* of the medical device container 12 as shown in FIG. 2. As a result, when the medical device container 12 is taken out or removed from the storage container 14 by a transfer device 64 (see FIG. 7), a space exists for inserting an arm of the transfer device 64 into the step portion 28*a* of the medical device container 12. An upper part of the storage container 14 is open, by virtue of the transfer opening 38, and this allows the medical device container 12 to be inserted into and taken out from the storage container 14.

Further, a flange portion (flange) 46 is provided at an upper end portion of the storage container main body 36 in surrounding relation to the transfer opening 38. The flange portion 46 extends outwardly and widens outward from an upper end portion of the peripheral wall portion 44, and the second sealing member 16 can be joined to the upwardly facing surface of the flange portion 46.

The second sealing member 16 is made of a material having air permeability and an antibacterial property, and may be the same material as the above-described materials for fabricating the inner sheet 34 and the first sealing member 22. The second sealing member 16 may be configured as a rectangular sheet having a size that covers the entire area of the transfer opening 38 so that the open upper end of the storage container 14 is closed. The second sealing member 16 is detachably joined to the flange portion 46.

Next, the positioning structures 48 and 50 of the medical device package 10 of the present embodiment will be described. The medical device package 10 is provided with the positioning structures 48 and 50 so as to reliably perform or permit opening and taking-out of the medical device container 12 at the time of being carried into the drug filling device 60. The first positioning structure 48 is a structure to position the medical device container 12 inside the storage container 14, and the second positioning structure 50 is a structure to position the storage container 14 and the transfer device 64.

Figure 4:
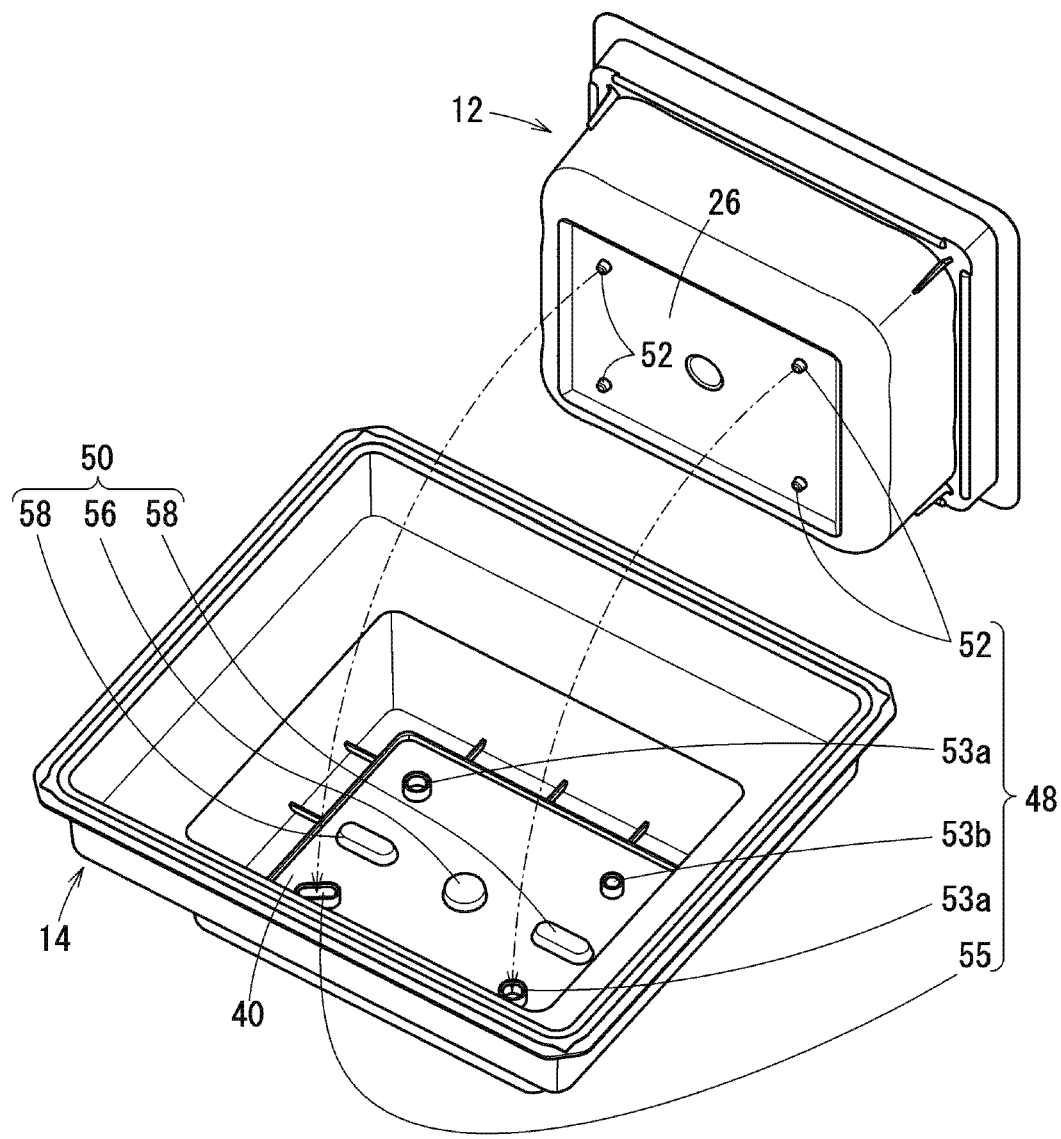
FIG. 4 is an explanatory view of a first positioning structure of a storage container of FIG. 1.

As illustrated in FIG. 4, the first positioning structure 48 includes four protruding portions (protrusions) 52 provided on the bottom portion 26 side of the medical device container 12, and concave portions (recesses) 53a and 53b and a rotation restricting portion 55 provided on the support portion 40 side of the storage container 14. The protruding portions 52 are formed as columnar protrusions, and are provided near four corners of the bottom portion 26 of the medical device container 12, respectively.

On the other hand, the pair of concave portions 53a positioned on one diagonal line, and the concave portion 53b and the rotation restricting portion 55 positioned on the other diagonal line are provided on the support portion 40 side of the storage container 14. The concave portions 53a and 53b and the rotation restricting portion 55 are arranged near four corners of the support portion 40, respectively, and are provided so as to correspond to the protruding portions 52. With respect to the three concave portions 53a and 53b, an inner diameter of one concave portion 53b located diagonally of the rotation restricting portion 55 is slightly larger than an outer diameter of the protruding portion 52. In order to absorb or account for manufacturing errors at the respective positions of the protruding portions 52, the inner diameters of the other two concave portions 53a are preferably larger, by an amount that anticipates the manufacturing errors or tolerances, than the outer diameter of the protruding portions 52.

The rotation restricting portion 55 includes a groove portion (groove) that is elongated diagonally in the support portion 40. Since the rotation restricting portion 55 is formed in a groove shape, the protruding portion 52 can be inserted into the rotation restricting portion 55 even when the positional relationship of the protruding portion 52 varies due to the manufacturing error. A width of the rotation restricting portion 55 is dimensioned or sized to be close to the outer diameter of the protruding portion 52, and is provided in a portion or location corresponding to one protruding portion 52. When the protruding portion 52 is inserted into the rotation restricting portion 55, axial rotation in a direction perpendicular to the bottom portion 26 of the medical device container 12 is restricted. Further, the concave portion 53b arranged diagonally of the rotation restricting portion 55 determines a horizontal position of the storage container 14 with respect to the support portion 40. That is, the medical device container 12 is substantially positioned on plane coordinates at two locations of the rotation restricting portion 55 and the concave portion 53b on the diagonal line. In addition, the other two concave portions 53a function as a base to maintain parallelism of the medical device container 12 with respect to the support portion 40. The concave portion 53a is not necessarily circular, and may have various shapes such as a rectangular shape. The medical device container 12 is positioned with respect to the storage container 14 by the above first positioning structure 48.

As illustrated in FIG. 5, the second positioning structure 50 is constituted by concave portions (recesses) 56 and 58 formed in the support portion 40 of the storage container 14. The central concave portion 56 has a circular shape when viewed from the bottom surface side, and engages with a protrusion on the transfer device 64 side to position the storage container 14 in the horizontal direction. The two concave portions 58 are located on opposite sides of the central concave portion 56, respectively. The two concave portions 58 are arranged so as to line up with the concave portion 56. Each of the concave portions 58 is elongated in the array direction of the three concave portions 56 and 58. That is, the three concave portions 56, 58 are arranged in an array direction, and the two elongated concave portions are elongated in that same array direction. The two concave portions 58 restrict the rotational displacement of the storage container 14.

Next, a method for manufacturing the medical device package 10 of the present embodiment will be described.

Figure 6A:
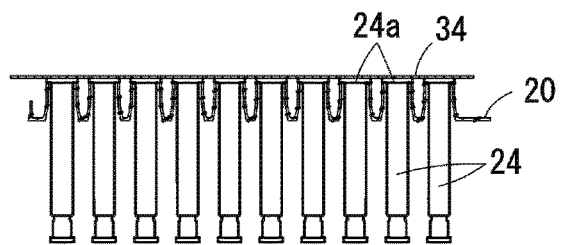
FIGS. 6A to 6D are explanatory views illustrating a method for manufacturing the medical device package of FIG. 1 in order of steps.
Figure 6B:
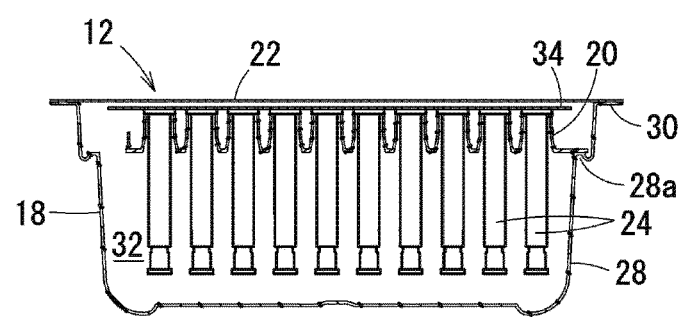

First, the syringes 24 are attached to the nest 20 as illustrated in FIG. 6A. Thereafter, the inner sheet 34 is placed so as to cover the filling openings 24b of the syringes 24. As illustrated in FIG. 6B, the inner sheet 34 may be placed in covering relation to the filling openings 24b after the nest 20 is accommodated in the medical device container main body 18.

Next, the nest 20 holding the syringes 24 is placed and set on the step portion 28a of the side wall 28 of the medical device container main body 18 as illustrated in FIG. 6B. Thereafter, the first sealing member 22 is joined to the flange portion 30 of the medical device container main body 18 to seal the accommodation space 32. The medical device container 12 is completed as above.

Figure 6C:
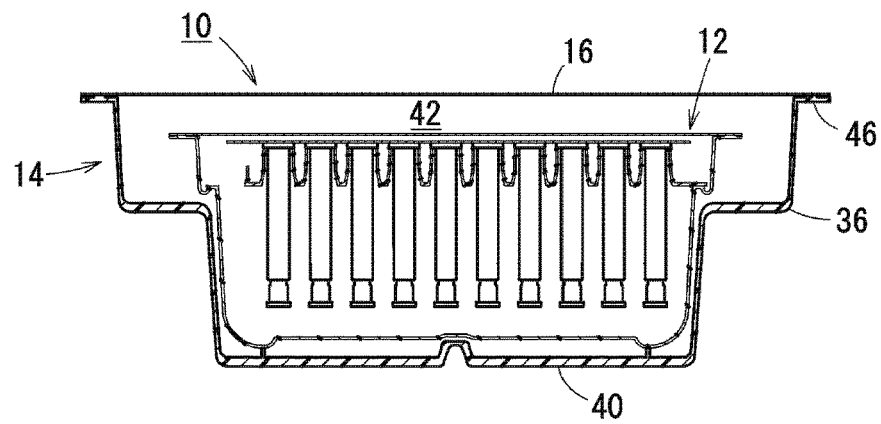

Next, the medical device container 12 is stored in the storage container main body 36 as illustrated in FIG. 6C. Thereafter, the second sealing member 16 is joined to the flange portion 46 of the storage container main body 36 to seal the accommodation space 42. As a result, the storage container 14 and the medical device package 10 are completed.

Figure 6D:
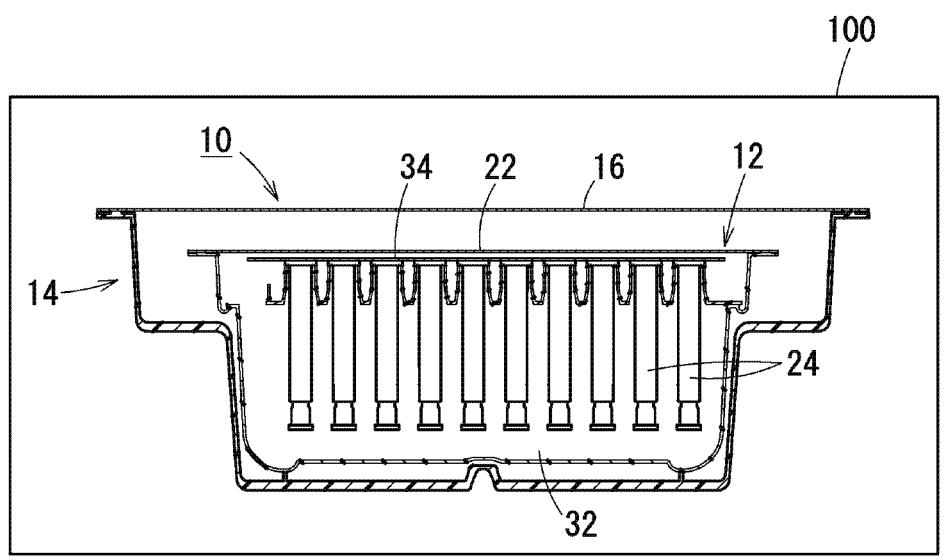

Thereafter, the storage container 14 is carried into a sterilizer 100 and sterilized using a gas or high-pressure water vapor as illustrated in FIG. 6D. Since the inner sheet 34, the first sealing member 22, and the second sealing member 16 are made of the material having the air permeability, the gas or high-pressure water vapor is supplied to the accommodation space 32 of the medical device container 12. As a result, the sterilization of the syringes 24 and the sterilization of the outer surface of the medical device container 12 can be performed at the same time. The sterilization processing is completed as above. Since the medical device container 12 is sealed inside the storage container 14, the outer surface of the medical device container 12 is kept in a sterilized state.

Hereinafter, an operation of the medical device package 10 of the present embodiment will be described.

As illustrated in FIG. 7, the medical device package 10 is carried into or moved into the drug filling device 60. In an opening unit 62 of the drug filling device 60, opening of the second sealing member 16 and carrying-out (removing) of the medical device container 12 in the medical device package 10 are performed. In the opening unit 62, the second sealing member 16 is peeled off from the storage container main body 36 by a suction device 63. Then, the medical device container 12 is carried out or removed from the storage container 14 by the transfer device 64.

Since the medical device container 12 is accommodated inside the storage container main body 36 which is sealed by the second sealing member 16, there is no risk of contamination due to a pinhole or the like in the medical device package 10 of the present embodiment. Therefore, the medical device container 12 is quickly taken out and transferred by the transfer device 64 without performing irradiation sterilization on the carried-in storage container 14. Since the storage container main body 36 having the shape-retaining property is used, there occur neither wrinkles nor changes in shape, and the medical device container 12 can be easily taken out. Further, the medical device container 12 is accurately positioned in the opening unit 62 by the first positioning structure 48 illustrated in FIG. 4 and the second positioning structure 50 illustrated in FIG. 5, and thus, can be reliably handled by the unattended (automated) transfer device 64.

As illustrated in FIG. 7, the medical device container 12 taken out from the storage container 14 is transferred to a medical device container opening unit 65 by the transfer device 64. In the medical device container opening unit 65, the first sealing member 22 is opened by a suction device 67. Thereafter, a nest transfer machine 66 carries out or removes the nest 20 holding the syringes 24 from the medical device container 12. The nest 20 is transferred to a filling unit 68. Then, the syringes 24 are filled with drugs and capped in the filling unit 68. Since the outer surface of the medical device container 12 is kept in the sterilized state in the drug filling device 60 as described above, it is possible to perform filling of the drug and capping without performing irradiation sterilization. As a result, the medical device package disclosed here can be suitably used for the drug filling device 60 that operates at high speed.

The medical device package 10 of the present embodiment has the following effects.

The medical device package 10 of the present embodiment includes: the medical device container 12 including the nest 20 which holds the plurality of medical devices (syringes 24) fillable with medicine to be aligned in a predetermined direction (e.g., the medical devices/syringes 24 are aligned in rows as generally shown in FIG. 3), the medical device container main body 18 which accommodates the nest 20, and the sheet-like or sheet-shaped first sealing member 22 that seals the medical device container main body 18; and the storage container 14 for packing with the outer peripheral surface of the medical device container 12 maintained in the sterile state. The storage container 14 includes: the storage container main body 36 accommodating the medical device container 12 and having the shape-retaining property; the transfer opening 38 formed at one end of the storage container main body 36 and configured to carry in and out the medical device container 12; and the sheet-like or sheet-shaped second sealing member 16 sealing the transfer opening 38 and having the antibacterial property and air permeability.

With the above configuration, the storage container 14 protects the medical device container 12 with the storage container main body 36 having the shape-retaining property, and thus, contamination due to a pinhole or the like can be prevented, so that the sterilized state of the outer surface of the medical device container 12 can be maintained. As a result, the irradiation sterilization is not required, and the use in the high-speed drug filling device 60 is possible. Since the storage container main body 36 has the shape-retaining property, wrinkles or changes in shape do not occur, and it is thus possible to reliably perform the opening and carrying-out of the medical device container 12 in the unattended transfer device 64. As a result, it is possible to reduce an error occurrence frequency in the transfer device 64 and to improve an operating rate of the drug filling device 60.

In the medical device package 10 described above, the bottom portion 26 of the medical device container 12 may be supported by the support portion 40 of the storage container 14, and the bottom portion 26 of the medical device container 12 and the support portion 40 of the storage container 14 may be provided with the first positioning structure 48 that prevents the displacement of the medical device container 12. With this configuration, the position of the medical device container 12 is accurately determined, so that the transfer device 64 can reliably carry out or remove the medical device container 12.

In the medical device package 10 described above, the support portion 40 of the storage container 14 may be provided with the second positioning structure 50 configured to determine the position of the storage container 14 with respect to the drug filling device 60. With this configuration, the positioning accuracy of the medical device container 12 is further improved.

In the medical device package 10 described above, the transfer opening 38 may be provided above the medical device container 12, and the second sealing member 16 may be positioned in opposing relation to the first sealing member 22 so that the second sealing member 16 and the first sealing member 22 are parallel to one another. With this configuration, water vapor that has passed through the second sealing member 16 quickly reaches the inside of the medical device container 12 through the first sealing member 22, so that high-pressure water vapor sterilization can be performed more quickly.

Second Embodiment

Figure 8A:
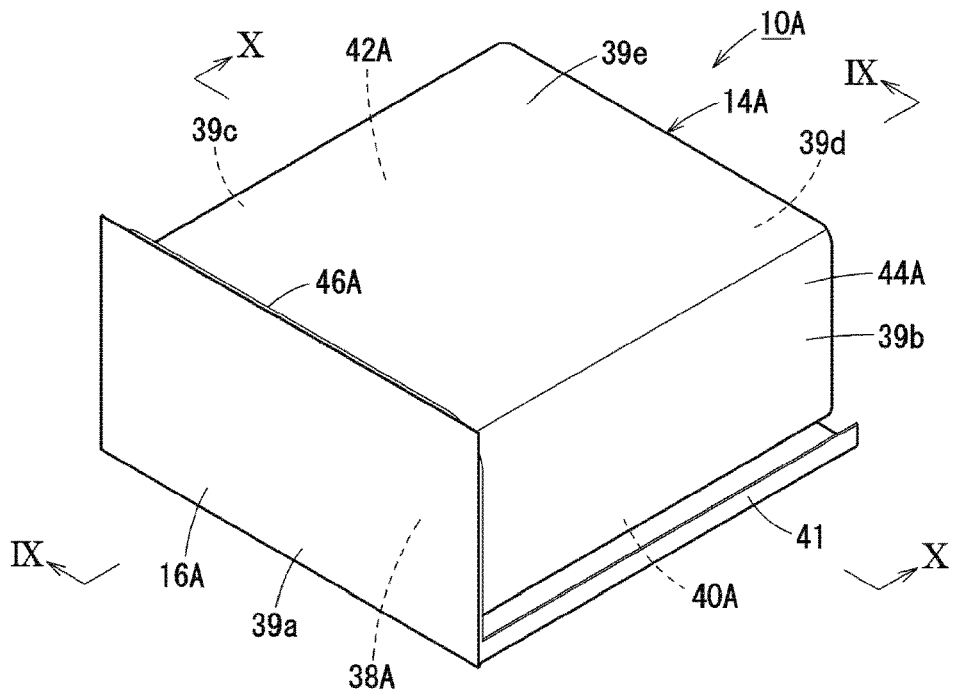
FIG. 8A is a perspective view of the front side of a medical device package according to a second embodiment.
Figure 8B:
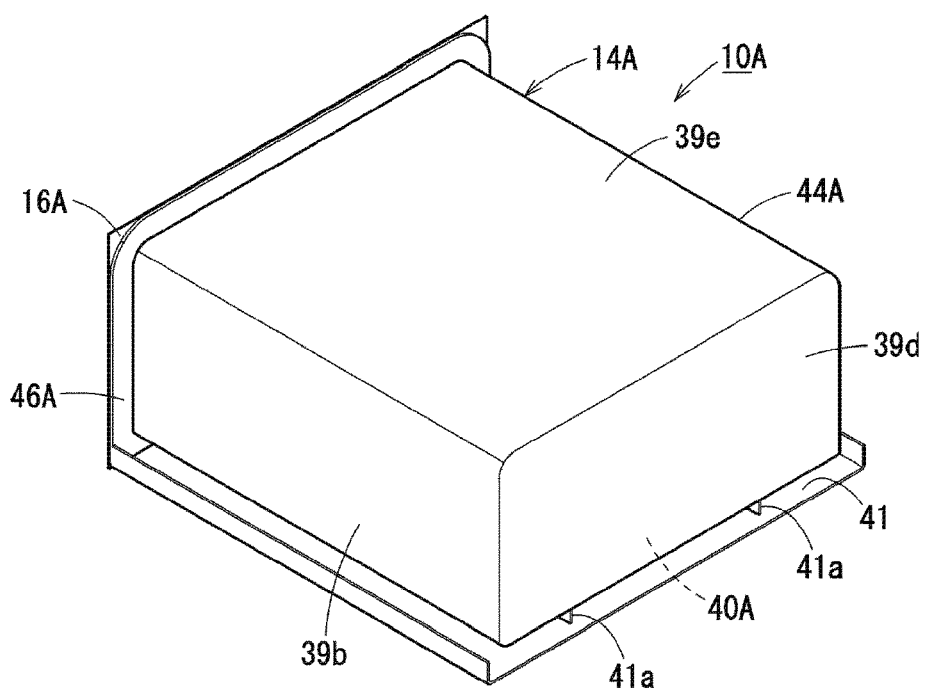
FIG. 8B is a perspective view of the back side of the medical device package of FIG. 8A.

As illustrated in FIGS. 8A and 8B, a medical device package 10A according to another embodiment includes a storage container 14A having a transfer opening (through opening) 38A on the lateral side, and a second sealing member 16A sealing the transfer opening 38A.

Figure 9:
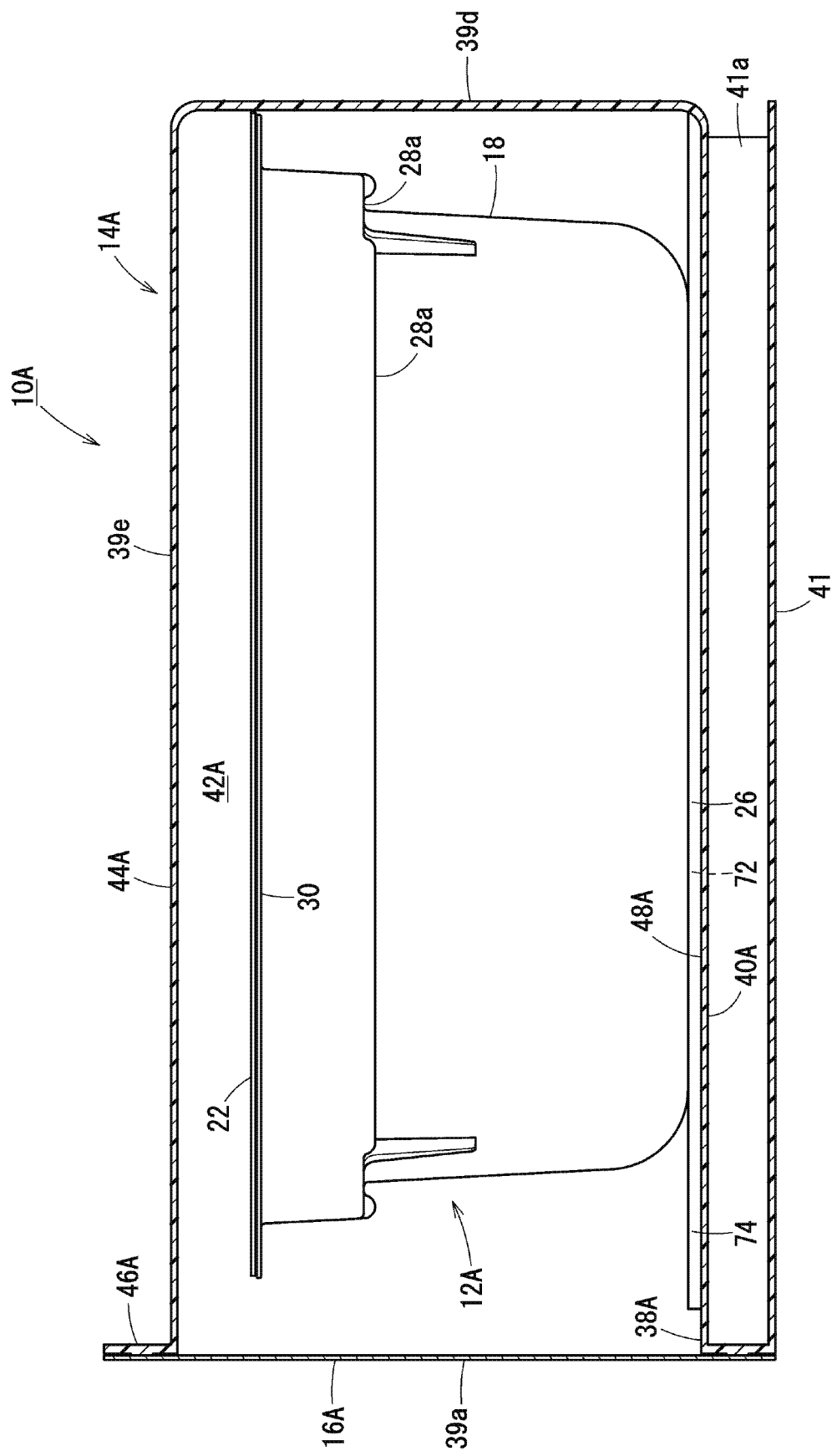
FIG. 9 is a cross-sectional view of the medical device package of FIG. 8A along line IX-IX.

As illustrated in FIG. 9, the storage container 14A has a support portion 40A that supports a medical device container 12A from below, and a peripheral wall portion 44A that is integrally formed with the support portion 40A. As illustrated in FIGS. 8A and 8B, the peripheral wall portion 44A is formed in a rectangular parallelepiped shape that is flat in the height direction and has side surfaces 39b and 39c, a back surface 39d, and an upper surface 39e. The peripheral wall portion 44A covers the upper side, the lateral sides, and the back side of the medical device container 12A. Further, the transfer opening 38A configured to permit the medical device container 12A to be introduced into and removed from the storage container 14A is formed on a front surface 39a side of the storage container 14A. As illustrated in FIG. 9, a flange portion 46A is formed around the transfer opening 38A. The flange portion 46A is formed along a plane perpendicular to the support portion 40A. As the second sealing member 16A is joined to the flange portion 46A, an accommodation space 42A of the storage container 14A is sealed.

The medical device container 12A is accommodated inside the accommodation space 42A. The medical device container 12A has the same structure as the medical device container 12 of the first embodiment, and the upper part is sealed by the first sealing member 22.

Figure 10:
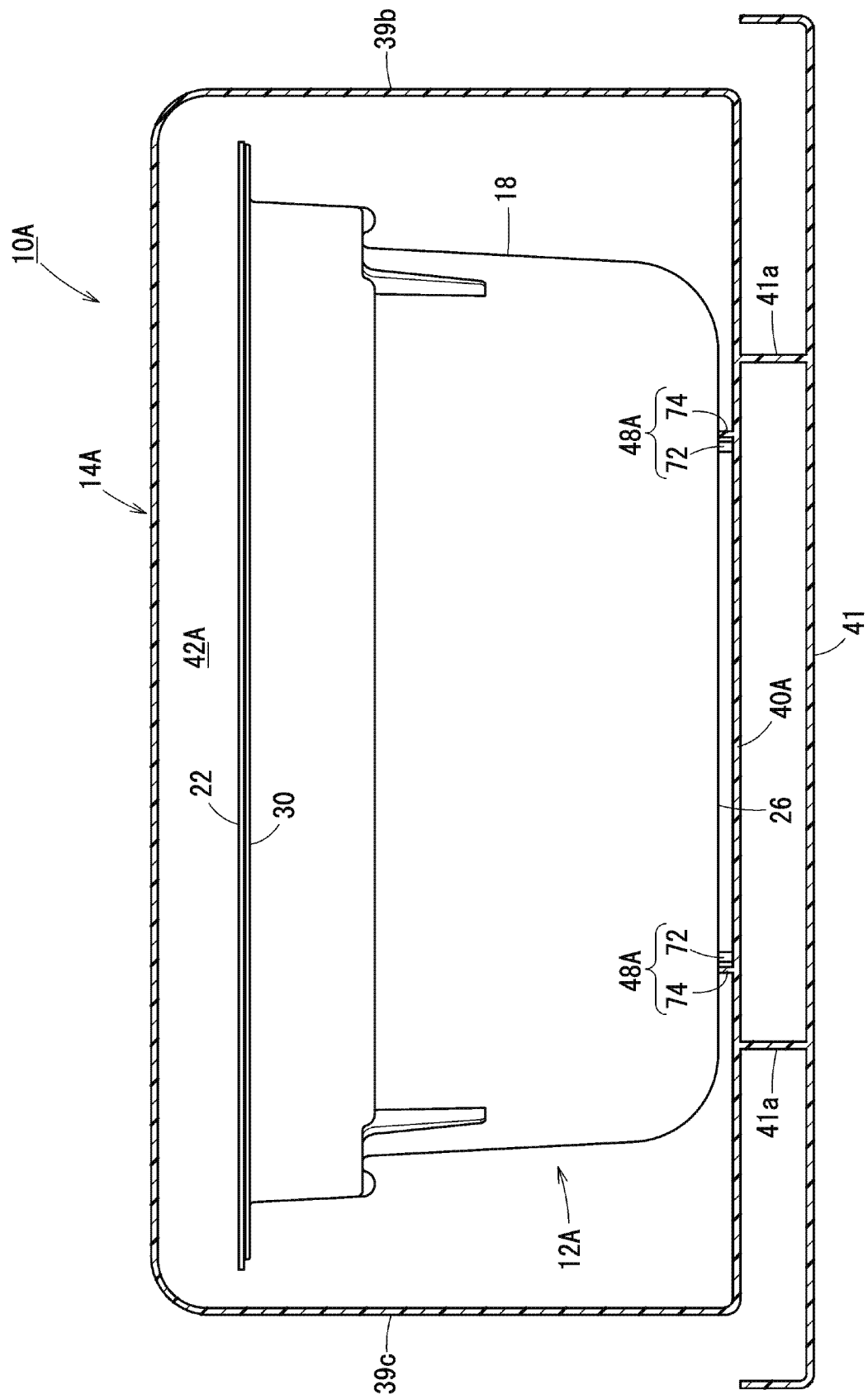
FIG. 10 is a cross-sectional view of the medical device package of FIG. 8A along line X-X.

A first positioning structure 48A of the medical device container 12A and the storage container 14A of the present embodiment includes a pair of rib-shaped protrusions 72 protruding downward from the bottom portion 26 of the medical device container 12A and a pair of rib-shaped protrusions 74 protruding upward from the support portion 40A of the storage container 14A as illustrated in FIG. 10. As illustrated in FIG. 9, the rib-shaped protrusions 72 and 74 extend in a direction toward a back surface 39d from the front surface 39a where the transfer opening 38A is formed. As illustrated in FIG. 10, the pair of rib-shaped protrusions 74 on the storage container 14A side are arranged to be separated in the width direction (i.e., the rib-shaped protrusions 74 are spaced apart from one another in the width direction (the left-right direction in FIG. 10)), and the rib-shaped protrusions 72 on the medical device container 12A side are provided so as to slide on the rib-shaped protrusions 74. According to the first positioning structure 48A of the present embodiment, the medical device container 12A is guided by the rib-shaped protrusions 72 and 74 at the time of moving the medical device container 12A into and out of the transfer opening 38A, and thus, the medical device container 12A can be moved in and out more smoothly.

Further, a pedestal 41 is provided below the support portion 40A in the storage container 14A of the present embodiment. The pedestal 41 is connected to the support portion 40A via a rib structure 41a. The pedestal 41 and the support portion 40A are separated via the rib structure 41a, thereby forming a gap for inserting the arm of the transfer device 64. As a result, it is unnecessary to provide the storage container 14A with the step portion 44b (see FIG. 2) protruding outward, and the storage container 14A can be further miniaturized.

The medical device package 10A of the present embodiment is configured as described above, and has the following effects.

In the medical device package 10A, the transfer opening 38A is provided on the lateral side of the medical device container 12A (the front surface 39a side), and the second sealing member 16A is arranged in a direction perpendicular to the first sealing member 22. According to the medical device package 10A of the present embodiment, the arm of the transfer device 64 can be inserted into the step portion 28a of the medical device container 12A from the lateral side of the medical device container 12A. As a result, it is unnecessary to provide the storage container 14A with the step portion 44b (see FIG. 2) protruding outward, and thus, the storage container 14A can be further miniaturized.

Third Embodiment

Figure 11A:
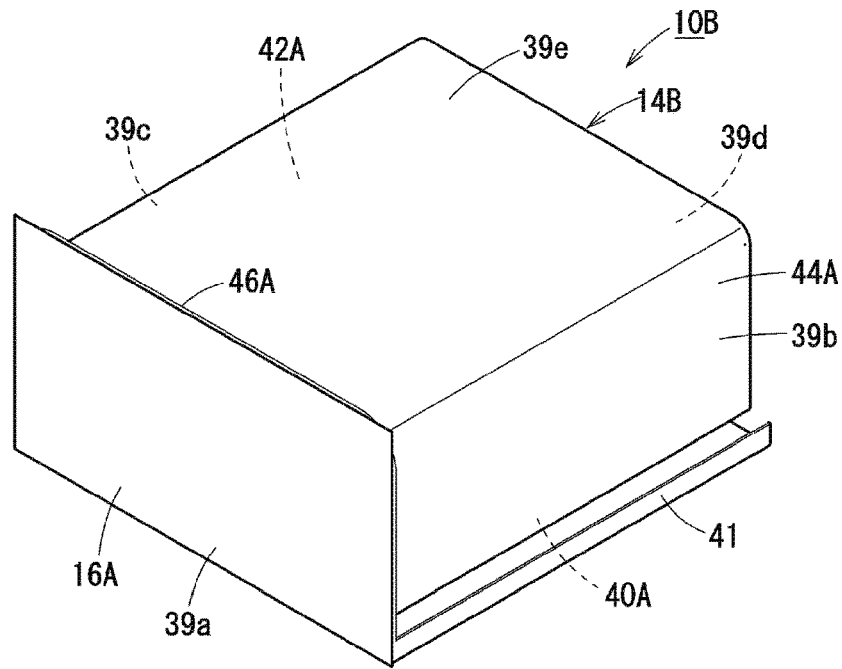
FIG. 11A is a perspective view of the front side of a medical device package according to a third embodiment.
Figure 11B:
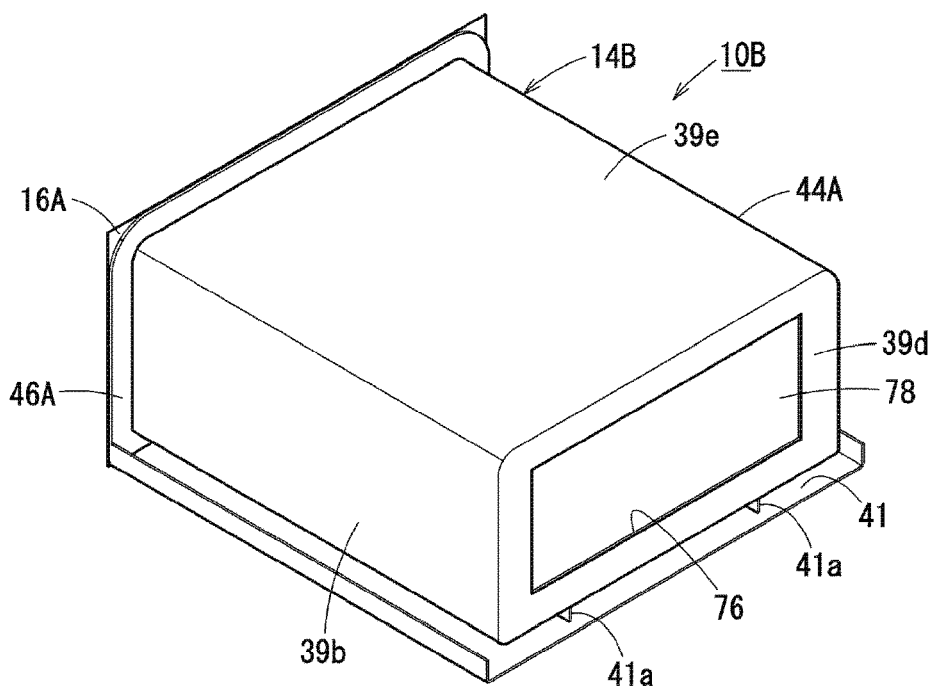
FIG. 11B is a perspective view of the back side of the medical device package of FIG. 11A.

As illustrated in FIGS. 11A and 11B, a medical device package 10B of another embodiment involves a modification of the medical device package 10A of the second embodiment illustrated in FIGS. 8A and 8B. In the medical device package 10B, the same components as those in the medical device package 10A are denoted by the same reference characters, and a detailed description of such components is not repeated.

The medical device package 10B of the present embodiment includes a storage container 14B formed in a rectangular parallelepiped shape that is flat in the height direction. As illustrated in FIG. 11B, a vent 76 formed by cutting out a large rectangular shape to form a through hole is formed on a back surface 39d of the storage container 14B. The vent 76 is sealed by a third sealing member 78.

Figure 12:
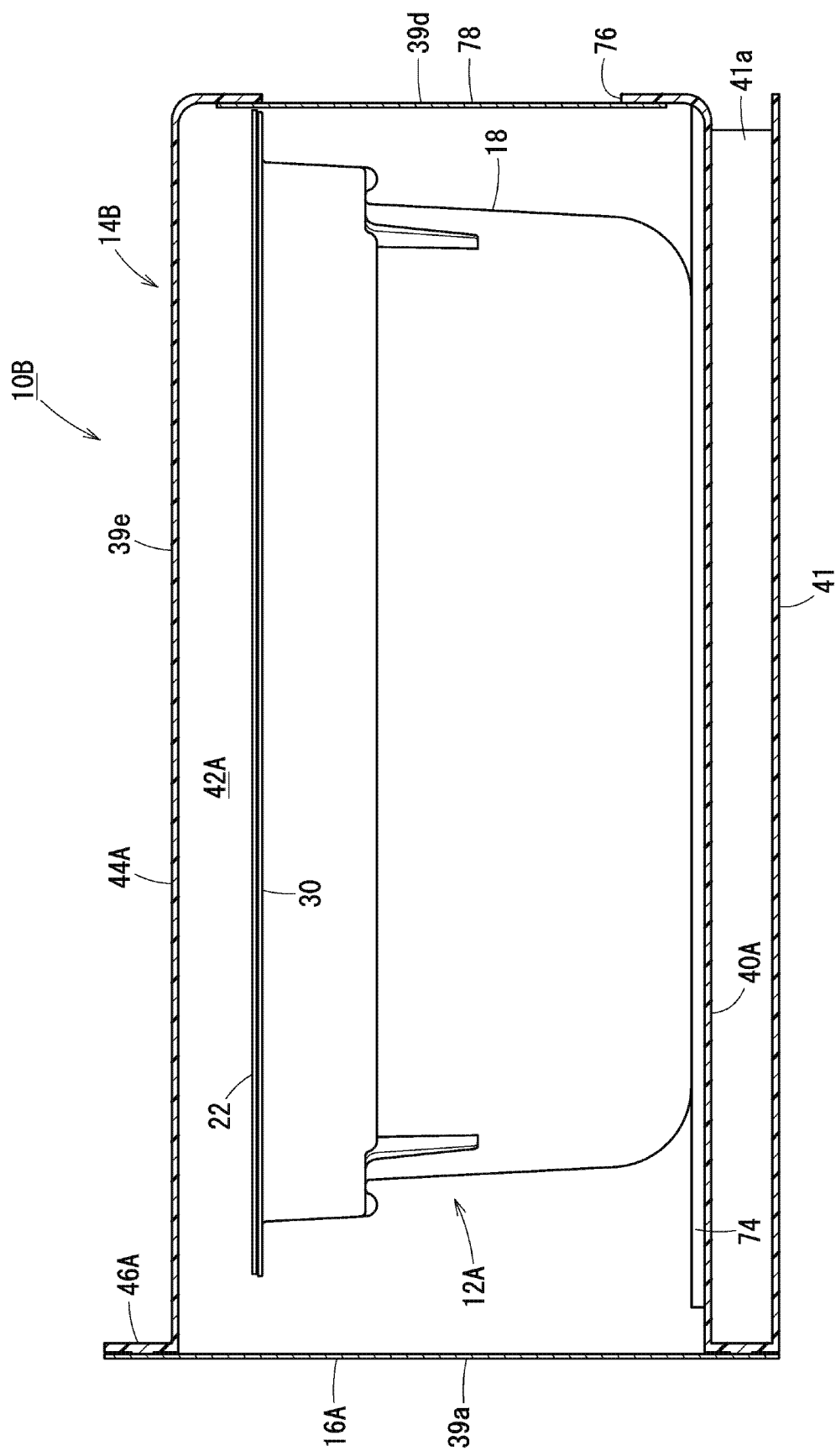
FIG. 12 is a cross-sectional view of the medical device package of FIG. 11A.

As illustrated in FIG. 12, the third sealing member 78 is joined to the back surface 39d of the storage container 14B from the inner side of the storage container 14B. As a result, it is possible to prevent the possibility that the third sealing member 78 is accidentally peeled off. The third sealing member 78 of the present embodiment is made of a sheet material having air permeability and an antibacterial property. Specifically, the same material as those of the first sealing member 22 and the second sealing member 16A can be used.

According to the medical device package 10B of the present embodiment, a gas and water vapor during sterilization can flow into the storage container 14B through the second sealing member 16A on the front surface 39a and the third sealing member 78 on the back surface 39d. That is, the opening area is increased in the medical device package 10B of the present embodiment, and thus, a flow rate of the gas and water vapor during sterilization is improved, the sterilization of the syringe 24 is improved, and the sterilization processing can be performed faster as compared with the medical device package 10A of the second embodiment.

The detailed description above describes embodiments of a medical device package representing examples of the inventive medical device package disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device package comprising:
a nest in which are held plural medical devices each of which is to be filled with medicine, each of the plural medical devices having an open upper end and a closed bottom end;
a medical device container main body that includes an accommodation space in which is positioned the nest and the plural medical devices, the accommodation space of the medical device container main body being surrounded by a bottom of the medical device container main body and by an upstanding side wall of the medical device container main body that extends upwardly away from the bottom of the medical device container main body, the medical device container main body including an opening that communicates with the accommodation space of the medical device container main body to permit the nest and the medical devices to be introduced into the accommodation space of the medical device container main body and to be removed from the accommodation space of the medical device container main body;
a sheet-shaped first seal covering the opening in the medical device container main body to seal the medical device container main body, the sheet-shaped first seal being removable to uncover the opening in the medical device container main body and permit the nest and the medical devices to be removed from the accommodation space of the medical device container main body;
a storage container main body that includes an accommodation space in which is positioned the medical device container main body in a sterile state, the accommodation space of the storage container main body being surrounded by a support portion of the storage container main body and an upstanding peripheral wall portion of the storage container main body that extends upwardly away from the support portion of the storage container main body, the support portion of the storage container main body facing the bottom of the medical device container main body, the storage container main body including an opening that communicates with the accommodation space of the storage container main body to permit the medical device container main body to be introduced into the accommodation space of the storage container main body and to be removed from the accommodation space of the storage container main body;

a sheet-shaped second seal covering the opening in the storage container main body to seal the storage container main body, the sheet-shaped second seal being removable to uncover the opening in the storage container main body and permit the medical device container main body to be removed from the accommodation space of the storage container main body;

the open upper ends of the plural medical devices being closed and sealed by a sheet-shaped seal member; and the sheet-shaped second seal having an antibacterial property and being air permeable.

2. The medical device package according to claim 1, wherein the opening in the medical device container main body is positioned at an upper end of the upstanding side wall of the medical device container main body, the sheet-shaped first seal that covers the opening in the medical device container main body being positioned in opposing relation and parallel to the sheet-shaped seal member that closes and seals the open upper ends of the medical devices.

3. The medical device package according to claim 1, wherein the upstanding side wall of the medical device container main body includes a step, an outer peripheral portion of the nest being supported on the step of the medical device container main body so that a bottom end of each of the plural medical devices is spaced from the bottom of the medical device container main body.

4. The medical device package according to claim 1, wherein the opening in the medical device container main body is positioned at an upper end of the upstanding side wall of the medical device container main body, the sheet-shaped first seal that covers the opening in the medical device container main body being positioned in overlying relation to the upper ends of the medical devices.

5. The medical device package according to claim 1, wherein the opening in the storage container main body that communicates with the accommodation space of the storage container main body is positioned at the upstanding peripheral wall portion of the storage container main body, the second seal that covers the opening in the storage container main body being positioned in opposing relation to the upstanding side wall of the medical device container main body.

6. The medical device package according to claim 1, wherein the support portion of the storage container main body rests on a part of the medical device storage container main body.

7. The medical device package according to claim 1, wherein the opening in the storage container main body that communicates with the accommodation space of the storage container main body is a first opening, the storage container main body including a second opening that communicates with the accommodation space of the storage container main body, and a sheet-shaped third seal that closes and seals the second opening in the storage container main body, the third seal being made of a material having an antibacterial property and air permeability.

8. The medical device package according to claim 1, wherein the through opening is provided on a lateral side of the medical device container, and the second sealing member is positioned perpendicular to the first sealing member.

9. The medical device package according to claim 8, wherein the through opening is a first through opening, the storage container including a second through opening on a surface of the storage container different from a surface of the storage container on which the first through opening is located, and a sheet-shaped third sealing member sealing the second through opening, and the third sealing member being made of a material having an antibacterial property and air permeability.

10. A medical device package comprising:

a nest in which are held plural medical devices each of which is to be filled with medicine, each of the plural medical devices having an open upper end and a closed bottom end;

a medical device container main body that includes an accommodation space in which is positioned the nest and the plural medical devices, the accommodation space of the medical device container main body being surrounded by a bottom of the medical device container main body and by an upstanding side wall of the medical device container main body that extends upwardly away from the bottom of the medical device container main body, the medical device container main body including an opening that communicates with the accommodation space of the medical device container main body to permit the nest and the medical devices to be introduced into the accommodation space of the medical device container main body and to be removed from the accommodation space of the medical device container main body;

a sheet-shaped first seal covering the opening in the medical device container main body to seal the medical device container main body, the sheet-shaped first seal being removable to uncover the opening in the medical device container main body and permit the nest and the medical devices to be removed from the accommodation space of the medical device container main body;

a storage container main body that includes an accommodation space in which is positioned the medical device container main body in a sterile state, the accommodation space of the storage container main body being surrounded by a support portion of the storage container main body and an upstanding peripheral wall portion of the storage container main body that extends upwardly away from the support portion of the storage container main body, the support portion of the storage container main body facing the bottom of the medical device container main body, the storage container main body including an opening that communicates with the accommodation space of the storage container main body to permit the medical device container main body to be introduced into the accommodation space of the storage container main body and to be removed from the accommodation space of the storage container main body;

a sheet-shaped second seal covering the opening in the storage container main body to seal the storage container main body, the sheet-shaped second seal being removable to uncover the opening in the storage container main body and permit the medical device container main body to be removed from the accommodation space of the storage container main body;

the sheet-shaped second seal having an antibacterial property and being air permeable; and protrusions and recesses, the protrusions being positioned on either the support portion of the storage container main body or the bottom of the medical device container main body, and the recesses on either the support portion of the storage container main body or the bottom of the medical device container main body, the protrusions being positioned in the recesses to position the medical device container main body at a predetermined position in the storage container main body.

11. The medical device package according to claim 10, wherein the open upper ends of the plural medical devices are closed and sealed by a sheet-shaped seal member.

12. The medical device package according to claim 10, wherein the recesses include recesses positioned adjacent corners of the support portion of the storage container main body or corners of the bottom of the medical device container main body, one of the recesses being an elongated recess that is elongated toward a diagonally opposite corner.

13. A medical device package comprising:
a nest in which are held plural medical devices each of which is to be filled with medicine, each of the plural medical devices having an open upper end and a closed bottom end;
a medical device container main body that includes an accommodation space in which is positioned the nest and the plural medical devices, the accommodation space of the medical device container main body being surrounded by a bottom of the medical device container main body and by an upstanding side wall of the medical device container main body that extends upwardly away from the bottom of the medical device container main body, the medical device container main body including an opening that communicates with the accommodation space of the medical device container main body to permit the nest and the medical devices to be introduced into the accommodation space of the medical device container main body and to be removed from the accommodation space of the medical device container main body;
a sheet-shaped first seal covering the opening in the medical device container main body to seal the medical device container main body, the sheet-shaped first seal being removable to uncover the opening in the medical device container main body and permit the nest and the medical devices to be removed from the accommodation space of the medical device container main body;
a storage container main body that includes an accommodation space in which is positioned the medical device container main body in a sterile state, the accommodation space of the storage container main body being surrounded by a support portion of the storage container main body and an upstanding peripheral wall portion of the storage container main body that extends upwardly away from the support portion of the storage container main body, the support portion of the storage container main body facing the bottom of the medical device container main body, the storage container main body including an opening that communicates with the accommodation space of the storage container main body to permit the medical device container main body to be introduced into the accommodation space of the storage container main body and to be removed from the accommodation space of the storage container main body;
a sheet-shaped second seal covering the opening in the storage container main body to seal the storage container main body, the sheet-shaped second seal being removable to uncover the opening in the storage container main body and permit the medical device container main body to be removed from the accommodation space of the storage container main body;
the sheet-shaped second seal having an antibacterial property and being air permeable; and
the support portion of the storage container main body including an inner surface facing towards the accommodation space of the storage container main body and an outer surface facing away from the accommodation space of the storage container main body, the outer surface of the support portion of the storage container main body including plural spaced-apart recesses configured to position the medical device storage container main body relative to a drug filling device.

14. A medical device package comprising:
a medical device container including a nest holding a plurality of medical devices aligned in a predetermined direction and configured to be filled with medicine, the medical device container also including a medical device container main body in which the nest is accommodated and a sheet-shaped first sealing member sealing the medical device container main body; and
a storage container;
the storage container including:
a storage container main body in which is accommodated the medical device container in a sterile state, the storage container main body having a shape-retaining property;
a through opening at one end of the storage container main body to permit the medical device container to be introduced into the storage container main body and to be removed from the storage container main body;
a sheet-shaped second sealing member sealing the through opening at the one end of the storage container main body, the sheet-shaped second sealing member having an antibacterial property and air permeability; and
the storage container including a support portion, a bottom portion of the medical device container being supported on the support portion of the storage container, and the bottom portion of the medical device container and the support portion of the storage container each include a positioning structure that engage one another and prevent displacement of the medical device container.

15. The medical device package according to claim 14, wherein the through opening is located above the medical device container, and the second sealing member is positioned in opposing relation to the first sealing member and parallel to the first sealing member.

16. A medical device package comprising:
a medical device container including a nest holding a plurality of medical devices aligned in a predetermined direction and configured to be filled with medicine, the medical device container also including a medical device container main body in which the nest is accommodated and a sheet-shaped first sealing member sealing the medical device container main body; and
a storage container;
the storage container including:
a storage container main body in which is accommodated the medical device container in a sterile state, the storage container main body having a shape-retaining property;
a through opening at one end of the storage container main body to permit the medical device container to be introduced into the storage container main body and to be removed from the storage container main body;
a sheet-shaped second sealing member sealing the through opening at the one end of the storage container main body, the sheet-shaped second sealing member having an antibacterial property and air permeability; and the storage container including a support portion, the support portion of the storage container including a positioning structure configured to position the storage container relative to a drug filling device.

17. The medical device package according to claim 16, wherein the storage container includes a support portion, a bottom portion of the medical device container being supported on the support portion of the storage container, and the bottom portion of the medical device container and the support portion of the storage container each include a positioning structure that engage one another and prevent displacement of the medical device container.

18. A medical device package comprising:

a nest in which are held plural upstanding medical devices each of which is to be filled with medicine, each of the plural medical devices having an open upper end and a closed bottom end;

a medical device container main body that includes an accommodation space in which is positioned the nest and the plural upstanding medical devices, the accommodation space of the medical device container main body being surrounded by a bottom of the medical device container main body and by an upstanding side wall of the medical device container main body that extends upwardly away from the bottom of the medical device container main body, the medical device container main body Including an opening at one end of the medical device container main body that communicates with the accommodation space of the medical device container main body to permit the nest and the medical devices to be introduced into the accommodation space of the medical device container main body and to be removed from the accommodation space of the medical device container main body;

a sheet-shaped first seal covering the opening at the one end of the medical device container main body to seal the medical device container main body, the sheet-shaped first seal including a surface facing the accommodation space of the medical device container main body and an opposite surface facing away from the accommodation space of the medical device container main body, the sheet-shaped first seal being removable to uncover the open upper end of the medical device container main body and permit the nest and the medical devices to be removed from the accommodation space of the medical device container main body;

a storage container main body that includes an accommodation space in which is positioned the medical device container main body in a sterile state sterilized by sterilization gas, the accommodation space of the storage container main body being surrounded by a support portion of the storage container main body and an upstanding peripheral wall portion of the storage container main body that extends upwardly away from the support portion of the storage container main body, the storage container main body including an opening at one end of the storage container main body to permit the medical device container main body to be introduced into the accommodation space of the storage container main body and to be removed from the accommodation space of the storage container main body, the storage container main body being made of a material possessing a shape-retaining property so that the storage container main body neither wrinkles nor changes in shape to facilitate removal of the medical device container main from the accommodation space of the storage container main body;

a sheet-shaped second seal covering the opening in the storage container main body to seal the storage container main body, the sheet-shaped second seal including a surface facing towards the medical device container main body, the surface of the sheet-shaped second seal being spaced from the sheet-shaped first seal and being spaced from the medical device container main body, the sheet-shaped second seal being removable from the storage container main body to uncover the opening in the storage container main body and permit the medical device container main body to be removed from the accommodation space of the storage container main body;

the sheet-shaped second seal having an antibacterial property and being air permeable by way of which the medical device container main body positioned in the storage container main body is sterilized by the sterilization gas; and protrusions and recesses, the protrusions being positioned on either the support portion of the storage container main body or the bottom of the medical device container main body, and the recesses being positioned on either the support portion of the storage container main body or the bottom of the medical device container main body, the protrusions being positioned in the recesses to position the medical device container main body at a predetermined position in the storage container main body, each of the recesses possessing a shape, the shape of at least one of the recesses being different from the shape of others of the recesses.

19. The medical device package according to claim 18, wherein the sheet-shaped first seal that covers the opening at the one end of the medical device container main body has an antibacterial property and is air permeable allowing sterilization of the nest by the sterilization gas.

20. The medical device package according to claim 19, wherein the plural medical devices are sterilized by the sterilization gas, the open upper ends of the plural medical devices being closed and sealed by a sheet-shaped seal member that has an antibacterial property and that is air permeable by way of which the plural medical devices are sterilized by the sterilization gas.

* * * * *